United States Patent [19]

Nozaki et al.

[11] Patent Number: 4,618,724

[45] Date of Patent: Oct. 21, 1986

[54] PERFLUOROCARBON POLYMER OXIDATION CATALYST AND PREPARATION OF CARBONYL COMPOUND

[75] Inventors: Hitosi Nozaki, Takatsuki; Koichiro Oshima, Kyoto, both of Japan

[73] Assignee: E. I. Du Pont de Nemours and Company, Wilmington, Del.

[21] Appl. No.: 700,655

[22] Filed: Feb. 11, 1985

[30] Foreign Application Priority Data

Feb. 28, 1984 [JP] Japan ................... 59-35321

[51] Int. Cl.$^4$ ............................................. C07C 45/29
[52] U.S. Cl. .................................. 568/311; 568/342; 568/385; 568/322; 568/361; 568/404
[58] Field of Search ............... 568/311, 342, 385, 322, 568/361, 404, 403; 502/159

[56] References Cited

U.S. PATENT DOCUMENTS

| | | | |
|---|---|---|---|
| 2,444,924 | 7/1948 | Farkas et al. | 568/404 |
| 2,861,045 | 11/1958 | Langer | 502/159 |
| 4,179,403 | 12/1979 | Kim et al. | 502/159 |
| 4,426,534 | 1/1984 | Guziec | 568/404 |
| 4,438,269 | 3/1984 | Guziec | 568/322 |
| 4,480,135 | 10/1984 | Esposito et al. | 568/342 |

OTHER PUBLICATIONS

Frechet et al, J. Org. Chem., vol. 43, pp. 2618-2621 (1978).

*Primary Examiner*—James H. Reamer

[57] ABSTRACT

This invention deals with the use of a perfluorocarbon polymer oxidation catalyst consisting of a perfluorocarbon main chain and a side chain constructed from structural units of chromium (III) difluoromethylene sulfonate or cerium (IV) difluoromethylene sulfonate in a method of preparing a carbonyl compound through an oxidation of an alcohol.

3 Claims, No Drawings

PERFLUOROCARBON POLYMER OXIDATION CATALYST AND PREPARATION OF CARBONYL COMPOUND

BACKGROUND OF THE INVENTION

This invention deals with oxidation of organic compounds using a perfluorocarbon polymer oxidation catalyst consisting of a perfluorocarbon main chain and a side chain constructed from structural units of chromium (III) difluoromethylene sulfonate or cerium (IV) difluoromethylene sulfonate, and particularly a method of preparing organic carbonyl compounds by oxidation of an alcohol in the presence of the aforementioned catalyst.

The oxidation of alcohols to produce carbonyl compounds such as aldehydes, carboxylic acids and ketones has been used in industry and laboratories alike. Since this oxidation does not proceed well with an organic peroxide, it is normally carried out in the presence of an inorganic oxidizing agent with a strong oxidizing power such as chromium (VI). One of the problems of using chromium (VI) as the oxidizing agent for the oxidation of an alcohol is the fact that it produces a rubbery precipitate. Another problem of using chromium (VI) as the oxidizing agent is the fact that the aldehyde, carboxylic acid or ketone formed cannot be separated from each other without difficulty, which results in lower yields of the desired products. Furthermore, the oxidation uses at least the chemical stoichiometric amount of chromium (VI), which means that a large amount of expensive and toxic chromium (VI) is involved in the process. This is a serious problem economically and also from the standpoint of industrial waste.

J. M. S. Frechet et. al. reported that poly (vinyl-pyridinium chlorochromate) can be used as the oxidizing agent for the alcohol. (*Journal of Organic Chemistry*, 43, 2618 (1978).) Although this method successfully prevented the formation of the rubbery precipitate, it had problems. For example, the exchange capacity of poly(vinyl pyridinium chlorochromate) was low and a large amount of polyvinyl pyridinium had to be used. When polyvinyl pyridinium was used as an oxidizing agent, the compound deteriorated and it was difficult to reuse the compound. Even when the compound could be reused, the oxidation reduced the chromium to (III) or (IV) and it had to be ion exchanged with chromium (VI) before it could be used again.

SUMMARY OF THE INVENTION

Surprisingly, chromium (III) and cerium (IV) which are only weak oxidizing agents or do not have any oxidizing power at all have now been discovered to be effective in catalyzing the production of carbonyl compounds through oxidation of alcohols when they were ion exchanged with a perfluorocarbon polymer consisting of a perfluorocarbon main chain and a side chain constructed from structural units of difluoromethylene sulfonic acid groups.

DETAILED DESCRIPTION OF THE INVENTION

The catalyst used in this invention is used in the production of carbonyl compounds by oxidation of alcohols with tertiary butyl hydroperoxide, cumene hydroperoxide, benzoyl peroxide or sodium bromate and is particularly effective in producing ketones from secondary alcohols. In other words, the catalyst used in this invention can replace the expensive and toxic chromium (VI) with an inexpensive non-toxic oxidizing agent which is not a problem in waste disposal. The catalyst used in this invention produces products in high yields without forming rubbery precipitate. Since the catalyst used in this invention is a solid, it can be easily separated from the liquid products. Furthermore, the catalyst used in this invention has a high oxidation resistance, chemical resistance such as solvent resistance and heat resistance, and can be used under severe reaction conditions. The catalyst used in this invention can also be regenerated and recycled. Thus, using the catalyst in this invention has many advantages.

The perfluorocarbon polymer (henceforth referred to as PFCP) which is the precurser of the catalyst used in this invention contains a difluoromethylene sulfonate group (i.e. a $CF_2SO_3X$ group where X is a cation) on the side chain. The catalyst of this invention replaces X on the side chain with chromium (III) or cerium (IV). (Henceforth, these ion exchanged materials will be referred to as Cr (III)/PFCP or Ce (IV)/PFCP.)

The aforementioned PFCP itself has been known widely as a fluorocarbon type ion exchange resin and its proton exchanged material or H/PFCP has been known as super strong acid. PFCP can be obtained from a copolymer of tetrafluoroethylene and a vinyl compound containing difluoromethylene sulfonyl fluoride group ($-CF_2SO_2F$) by heating it in an organic/aqueous solution containing NaOH or KOH to hydrolyze the $-CF_2SO_2F$ group to a difluoromethylene sulfonate group ($-CF_2SO_3X$; X is Na or K in this product).

The examples of typical vinyl comounds containing a difluoromethylene sulfonyl fluoride group are the compounds indicated by the following formulae

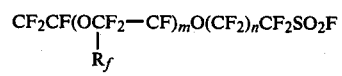

(in the formulae, n is a cardinal number of 0-3, m is a cardinal number of 1-3 and $R_f$ is F or $CF_3$).

The hydrolyzed polymer of PFCP is known by the trade name of Nafion ® (registered trade mark for Du Pont Co. perfluorinated ion exchange resin). The main chain in PFCP is the perfluorocarbon chain formed by tetrafluoroethylene and a vinyl group of the aforementioned vinyl compound. This polymer is highly resistant to heat and chemicals and it can be used under almost any reaction conditions. The active sites of the catalyst are chromium (III) difluoromethylene sulfonate and cerium (IV) difluoromethylene sulfonate on the ends of the side chains. Thus, the activity of the catalyst can be expressed by the weight (g) of PFCP per one mole of difluoromethylene sulfonic acid group or the equivalent weight (henceforth referred to as EW).

Although the EW of PFCP used as a catalyst in this invention is not specifically limited, it is preferably to have the EW less than 3000 and it is particularly preferable to have the EW between 900 and 1,500. The reason for this restriction is due to the small number of active sites available on the catalyst when EW of PFCP is too high. On the other hand, when EW is too low, the catalyst is soluble in polar solvents such as ethanol and this makes the separation of the reaction products more difficult.

The catlayst used in this invention can be formed by soaking a commercial K/PFCP or Na/PFCP in an aqueous solution of a Cr (III) salt or a Ce (IV) salt to substitute K or Na with Cr (III) or Ce (IV) by standard ion exchange methods. The ion exchange of K or Na does not have to have the entire K or Na substituted with Cr (III) or Ce (VI). For example, the activity of the catalyst with 50% ion exchanged is sufficient.

Cr (III)/PFCP is useful as a catalyst to obtain an aldehyde or a carboxylic acid from a primary alcohol in the presence of an oxidizing agent or to obtain a ketone from a secondary alcohol. On the other hand, Ce (IV)/PFCP is useful as a catalyst to obtain a ketone from a secondary alcohol but it is not effective as an oxidation catalyst with a primary alcohol. Thus, the aforementioned catalyst is very effective in obtaining a ketoalcohol from a dehydrogenative oxidation of the secondary hydroxyl group alone in a polyol containing a primary hydroxyl group and a secondary hydroxyl group.

For example, 10-ketoundecane-1-ol can be obtained from 1,10-undecane diol according to the equation

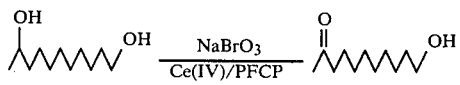

and 4-hydroxymethylcyclohexanone from 4-hydroxymethyl cyclohexanol according to the equation

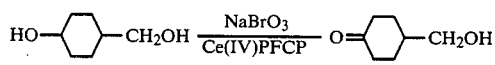

The yields of the desired products were 82% and 73%, respectively.

When an alcohol containing an unsaturated linkage in the molecule is oxidized using Ce (IV) as the oxidizing agent, the oxidation of the hydroxyl group was blocked by the unsaturated linkage. In contrast to this, when the same compound is oxidized using Ce (IV)/PFCP as a catalyst, the unsaturated linkage in the alcohol does not interfere with the reaction and the hydroxyl group alone is oxidized.

For example, when 2-cyclododecene-1-ol and 11-dodecene-2-ol are oxidized, the corresponding ketones are obtained in high yields of 82% and 80%.

The catalyst used in this invention is effective not only in the oxidation of alcohols. The catalyst is also effective in other oxidation reactions such as the oxidation reaction hydroquinone to quinone, and the oxidation reaction of sulfide to sulfoxide and sulfone.

This invention is explained with examples in the following paragraphs.

EXAMPLE A

To a solution prepared by dissolving 0.69 g of Cr(OAc)$_3$ in 30 ml of deionized water, 1.1 g of tetrafluoroethylene/potassium perfluoro(3,6-dioxa-4-methyl-7-octene)sulfonate copolymer (henceforth referred to as K/PFCP) EW=1,100 were added. The mixture was agitated for 36 hours at 25° C. to carry out the ion exchange process. The catalyst obtained was filtered and washed with deionized water. The catalyst was dried and the dried catalyst had 0.68 mmoles of Cr (III) adsorbed per one gram of the catalyst. The total exchange capacity of PFCP was 75% converted to Cr (III).

EXAMPLE B

In a solution prepared by dissolving 1.75 g of (NH$_4$)$_2$Ce(NO$_3$)$_6$ in 30 ml of deionized water, 1.1 g of K/PFCP was added. The mixture was agitated for 36 hours at 25° C. to carry out ion exchange process. The catalyst obtained was filtered, washed with deionized water and dried. The dried catalyst contained 0.54 mmoles of Ce (IV) adsorbed on each gram of the catalyst. This is an indication that 71% of the total exchange capacity of PFCP was exchanged with Ce (IV).

EXAMPLE 1

A suspension of 50 mg of Cr (III)/PFCP obtained in Example A in 1.0 ml of chlorobenzene was added to a solution of 0.12 g (1.0 mmole) of 1-phenylethanol in 2.0 ml of chlorobenzene. Next, a benzene solution of t-butyl hydroperoxide (2.64 M, 1.5 ml, 4.0 mmoles) was added and the entire mixture was heated for about seven hours at 85° C.

The catalyst was filtered and was washed with ethyl acetate. The filtrarte and the wash solution were combined and the combined solution was washed with an aqueous NaHSO$_3$ and salt solution. The concentrated product was purified by a silica gel column chromatograph to yield 0.11 g of acetophenone. The yield from the starting alcohol was 95%.

EXAMPLE 2

Using the same reaction conditions described in Example 1, 1 mmole of the alcohols listed in Table 1 was allowed to react with 4.0 mmoles of t-butyl hydroperoxide and 0.034 mmole of Cr (III)/PFCP to obtain the corresponding ketones. The yields based on the starting alcohols are shown in Table 1.

EXAMPLE 3

The oxidation reaction was carried out by using 4.0 mmoles of t-butyl hydroperoxide and 0.34 mmole of Cr (III)/PFCP per 1 mmole of 1-dodecanol at 80° C. for 12 hours. The yield of dodecanal was 39% and the yield of dodecanoic acid was 15%. The recovery of unreacted 1-dodecanol was 24%.

EXAMPLE 4

A benzene solution of 1.0 mmole of the alcohols listed in Table 2 and 4.0 mmoles of t-butyl hydroperoxide was used to disperse Ce (IV)/PFCP (50 mg, 0.027 mmole) obtained in Example 2. The dispersion was heated for six hours at 80° C. to obtain corresponding ketones. The yields are shown in Table 2.

EXAMPLE 5

To acetic acid in which Ce (IV)/PFCP (50 mg, 0.027 mmole) and 200 mg of NaBrO$_3$ were dispersed and dissolved, 1.0 mmole of 1,10-undecane diol and 1.0 mmole of 4-hydroxymethyl cyclohexanol were added, respectively. The reaction mixture was heated for three hours at 55° C. and the product was purified with a column chromatography to yield 154 mg (82% yield) of 10-undecane-1-ol and 93 mg (73% yield) of 4-hydroxymethyl cyclohexanone.

TABLE 1

| Name of alcohols | yield of ketone (%) |
| --- | --- |
| cyclododecanol | 86 |

TABLE 1-continued

| Name of alcohols | yield of ketone (%) |
|---|---|
| PhCH=CHCH(OH)CH$_3$ | 81 |
| 4-dodecanol | 81 |
| p-Cl—C$_6$H$_4$CH(OH)CH$_3$ | 93 |
| 4-t-butylcyclohexanol | 81 |
| PhCH(OH)CH$_3$ | 95 |
| Ph$_2$CHOH | 98 |

TABLE 2

| Name of alcohol | yield of ketone (%) |
|---|---|
| cyclododecanol | 82 |
| 2-cyclododecene-1-ol | 82 |
| 4-dodecanol | 71 |
| 3-undecanol | 79 |
| 4-t-butylcyclohexanol | 98 |
| PhCH(OH)CH$_3$ | 93 |
| 11-dodecene-2-ol | 80 |

We claim:

1. A method of oxidizing a secondary organic alcohol to form a ketone which comprises treating said alcohol with at least one oxidizing agent selected from the class consisting of tertiary butyl hydroperoxide, cumene hydroperoxide, benzoyl peroxide, and sodium bromate in the presence of a perfluorocarbon polymer consisting of a perfluorocarbon main chain and side chains containing terminal structural units of the formula

—CF$_2$SO$_2$X wherein X is chromium (III) or cerium (IV) wherein the weight in grams of the perfluorocarbon polymer per one mole of —CF$_2$SO$_2$X groups is between 900 and 3000, and wherein the polymer is present in catalytically effective amounts, for a time and temperature sufficient to produce said ketone.

2. The method of claim 1 wherein in the formula —CF$_2$SO$_2$X, X is chromium III.

3. The method of claim 1 wherein in the formula —CF$_2$SO$_2$X, X is cerium (IV).

* * * * *